United States Patent [19]

Graham et al.

[11] Patent Number: 5,238,922

[45] Date of Patent: Aug. 24, 1993

[54] INHIBITORS OF FARNESYL PROTEIN TRANSFERASE

[75] Inventors: Samuel L. Graham, Schwenksville; S. Jane deSolms, Norristown; Victor M. Garsky, Blue Bell, all of Pa.

[73] Assignee: Merck & Co., Inc., Rahway, N.J.

[21] Appl. No.: 770,078

[22] Filed: Sep. 30, 1991

[51] Int. Cl.$^5$ .......................... A61K 37/02; C07K 5/02
[52] U.S. Cl. ...................................... 514/18; 530/330; 530/332; 930/DIG. 780; 930/DIG. 787; 514/19; 514/562; 514/331; 562/426; 562/557
[58] Field of Search ............... 530/330, 332; 514/18, 514/19, 562, 331; 930/780, 787; 562/426, 557

[56] References Cited

U.S. PATENT DOCUMENTS 5,043,268  8/1991  Stock ..................................... 435/15

FOREIGN PATENT DOCUMENTS

0456180A1  11/1991  European Pat. Off. .
WO 91/16340  10/1991  PCT Int'l Appl. .

OTHER PUBLICATIONS

Reiss, et al., Proc. Natl. Acad. Sci. USA 88, 732-6 (1991).
Schaber, et al., J. Biol. Chem. 265, 14701-4 (1990).
Goldstein, J. L., et al., "Nonfarnesylated Tetrapeptide Inhibitors of Protein Farnesyltransferase", *The Journal of Biological Chemistry*, vol. 266, No. 24 pp. 15575-15578 (1991).

*Primary Examiner*—Jeffrey E. Russel
*Assistant Examiner*—Eric Linnell
*Attorney, Agent, or Firm*—Mark R. Daniel; Joseph F. DiPrima

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

21 Claims, No Drawings

INHIBITORS OF FARNESYL PROTEIN TRANSFERASE

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171-286 (1989). Forms of ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583-586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093-1098 (1989); Hancock et al., *Cell* 57: 1167-1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a substrate is responsible for Ras farnesylation. (Reiss et al., *Cell,* 62: 81-88 (1990); Schaber et al., *J. Biol. Chem.,* 265: 14701-14704 (1990); Schafer et al., *Science,* 249: 1133-1139 (1990); Manne et al., *Proc. Natl. Acad. Sci USA,* 87: 7541-7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86: 6630-6634 (1989)). Cytosol-localized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects such as interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibiting of farnesyl-protein transferase is more specific and is attended by fewer side effects than is the case for a general inhibitor of isoprene biosynthesis.

Previously, it has been demonstrated that tetrapeptides with the CAAX sequence inhibit Ras farnesylation (Schaber et al., ibid; Reiss et. al., ibid; Reiss et al., *PNAS,* 88: 732-736 (1991)). However, the reported inhibitors of farnesyl-transferase inhibitors are metabolically unstable or inactive in cells.

The novel compounds of this invention exhibit one or more reduced peptide bonds and are inhibitors of Ras farnesyl-transferase. The presence of the reduced amide linkages in the compounds of this invention confers metabolic stability to these inhibitors such that they are capable of inhibiting Ras farnesylation in vivo. The reduction of certain of the amide bonds in the compounds of this invention further leads to an unexpected enhancement of intrinsic enzyme-inhibitory activity.

It is, therefore, an object of this invention to develop compounds which will inhibit farnesyl-protein transferase and the farnesylation of the oncogene protein Ras. It is a further object of this invention to develop chemotherapeutic compositions containing the compounds of this invention, and methods for producing the compounds of this invention.

SUMMARY OF THE INVENTION

The present invention includes compounds which inhibit farnesyl-protein transferase and the farnesylation of the oncogene protein Ras, chemotherapeutic compositions containing the compounds of this invention, and methods for producing the compounds of this invention.

The compounds of this invention are illustrated by the formula:

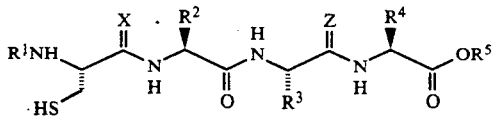

DETAILED DESCRIPTION OF THE INVENTION

The compounds of this invention are useful in the inhibition of farnesyl-protein transferase and the farnesylation of the oncogene protein Ras. The compounds of this invention are illustrated by the formula:

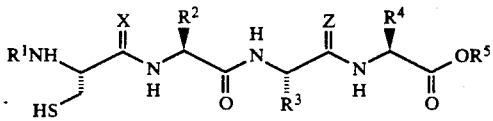

wherein:

X, Y and Z are independently $H_2$ or O, provided that at least one of these is $H_2$;

$R^1$ is H, an alkyl group, an acyl group, an alkylsulfonyl group or arylsulfonyl group, wherein alkyl and acyl groups comprise straight chain or branched chain hydrocarbons of 1 to 6 carbon atoms, or in the alternative, $R^1$NH may be absent;

$R^2$, $R^3$ and $R^4$ are the side chains of naturally occurring amino acids, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms, wherein the aliphatic substitutents may be substituted with an aromatic or heteroaromatic ring;

$R^5$ is H or a straight or branched chain aliphatic group, which may be substituted with an aromatic or heteroaromatic group;

or the pharmaceutically acceptable salts thereof.

The preferred compounds of this invention are as follows:

N-(3-phenyl-2(S)-(mercaptopropionylamino)prop-1-yl)isoleucyl-methionine,

N-(2(R)-amino-3-mercaptopropyl)isoleucyl-phenylalanyl-methionine,

N-(3-mercaptopropyl)isoleucyl-phenylalanyl-methionine,

N-(3-mercaptopropyl)valyl-isoleucyl-methionine,

N-(2(R)-amino-3-mercaptopropyl)valyl-isoleucyl-methionine,

N-(3-methyl-2(S)-(cysteinylamino)but-1-yl)phenylalanyl-methionine,

N-(3-methyl-2(S)-(mercaptopropionylamino)but-1-yl)-phenylalanyl-methionine,

N-[2(S)-(2(R)-amino-3-mercaptopropylamino)-3(S)methylpentyl]phenylalanyl-methionine, N-[2(S)-(3-mercaptopropylamino)-3(S)-methylpentyl]-phenylalanyl-methionine, N-(2(R)-amino-3-mercaptopropyl)isoleucyl-phenylalanyl-(methionine sulfone), N-(2(R)-amino-3-mercaptopropyl)isoleucyl-(p-iodophenylalanyl)-methionine.

N-[2(R)-(cysteinyl-isoleucylamino)-3(S)-methylpentyl]-methionine,

N-[2(R)-(N'-(2(R)-amino-3-mercaptopropyl)-isoleucylamino)-3-phenyl-propyl]methionine, N-[2(R)-(N'-(2(R)-amino-3-mercaptopropyl)-isoleucylamino)-3(S)-methylpentyl]methionine, N-(3-mercaptopropyl)valyl-isoleucyl-methionine methyl ester, N-(2(R)-amino-3-mercaptopropyl)isoleucyl-phenylalanyl-methionine ethyl ester, or N-(2(R)-amino-3-mercaptopropyl)isoleucyl-phenylalanyl-methionine benzyl ester.

The most preferred compounds of this invention are as follows:

N-[2(S)-(2(R)-amino-3-mercaptopropylamino)-3(S)-methylpentyl]phenylalanyl-methionine

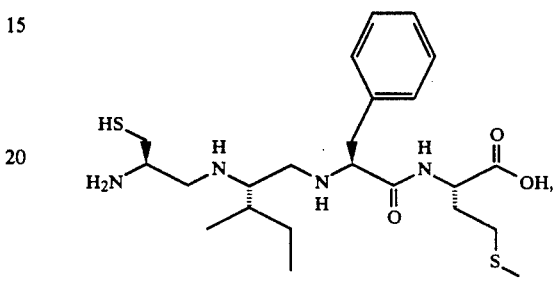

N-(3-methyl-2(S)-(cysteinylamino)but-1-yl)phenylalanylmethionine

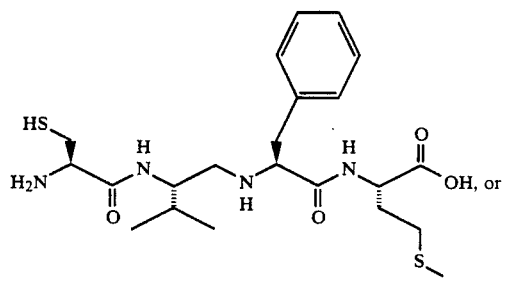

N-(2(R)-amino-3-mercaptopropyl)isoleucyl-phenylalanyl-methionine ethyl ester

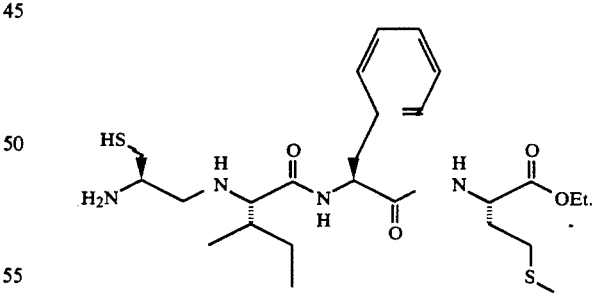

In the present invention, the amino acids are identified both by conventional 3 letter and single letter abbreviations as indicated below:

| | | |
|---|---|---|
| Alanine | Ala | A |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |

| | | |
|---|---|---|
| -continued | | |
| Glutamic acid | Glu | E |
| Glutamine or | Glx | Z |
| Glutamic acid | | |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, sali7 cylic, sulfanilic, 2-acetoxy-benzoic, fumaric, toluenesulfonic, methanesulfonic, ethane disulfonic, oxalic, isethionic, and the like.

The pharmaceutically acceptable salts of the compounds of this invention can be synthesized from the compounds of this invention which contain a basic moiety by conventional chemical methods. Generally, the salts are prepared by reacting the free base with stoi7 chiometric amounts or with an excess of the desired salt-forming inorganic or organic acid in a suitable solvent or various combinations of solvents.

The pharmaceutically acceptable salts of the compounds of this invention are also readily prepared by conventional procedures such as treating an acid of the compounds of this invention with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

The compounds of the invention can be synthesized from their constituent amino acids by conventional peptide synthesis techniques and additional methods described below. Standard methods of peptide synthesis are disclosed, for example, in the following works: Schroeder et al., "The peptides:, Vol. I. Academic Press 1965, or Bodanszky et al., "Peptide Synthesis", Interscience Publishers, 1966, or McOmie (ed.) "Protective Groups in Organic Chemistry", Plenum Press, 1973, or Baranyl et al., "The Peptides: Analysis, Synthesis, Biology" 2, Chapter 1, Academic Press, 1980, or Stewart et al., "Solid Phase Peptide Synthesis", Second Edition, Pierce Chemical Company, 1984. The teachings of these works are hereby incorporated by reference.

The compounds of this invention may be prepared according to the following reaction schemes:

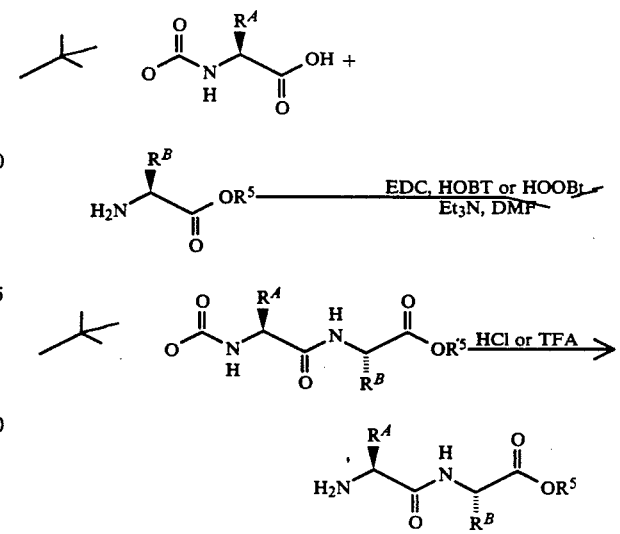

SCHEME 1
Reaction A. Coupling of residues to form an amide bond.

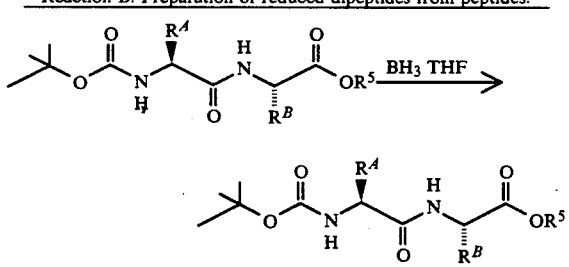

SCHEME 2
Reaction B. Preparation of reduced dipeptides from peptides.

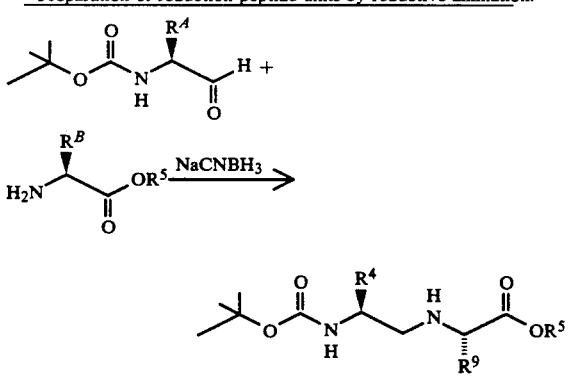

SCHEME 3
Reaction C:
Preparation of reduction peptide units by reductive amination.

Compounds of this invention are prepared by employing reactions A–C as shown in Schemes 1–3 above, in addition to other standard manipulations such as ester hydrolysis, cleavage of peptide protecting groups, etc., as may be known in the literature or exemplified in the Examples. The key bond-forming reactions are:

Reaction A. Peptide bond formation and protecting group cleavage using standard solution or solid phase methodologies.

Reaction B. Preparation of a reduced peptide subunit by borane reduction of the amide moiety.

Reaction C. Preparation of a reduced peptide subunit by reductive alkylation of an amine by an aldehyde using sodium cyanobrorhydride, hydrogen and a catalyst or other reducing agents.

These reactions may be employed in linear sequence to provide the compounds of the invention or they may be used to synthesize dipeptide fragments which are subsequently joined by the alkylation or acylation reactions described in the Schemes.

The compounds of this invention inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous, rectal and topical administration.

For oral use of a chemotherapeutic compound according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight of a mammal per day, preferably of between 0.5 mg/kg of body weight to about 10 mg/kg of body weight of a mammal per day.

EXAMPLES

Examples provided are intended to assist in a further understanding of the invention. Particular materials employed, species and conditions are intended to be further illustrative of the invention and not limitative of the reasonable scope thereof.

EXAMPLE 1

Preparation of N-(3-methyl-2(S)-(cysteinylamino)but-1-yl)phenylalanyl-methionine Step A. Preparation of N-(3-methyl-2(S)-(t-butoxycarbonylamino)but-1-yl)phenylalanine methyl ester Sodium cyanoborohydride (2.0 g, 0.03 mole) was added portionwise (one hour) to a solution of the known compound 2(S)-t-butoxycarbonylamino-3-methylbutyraldehyde (5.8 g, 0.029 mole) and phenylalanine methyl ester hydrochloride (6.1 g, 0.028 mole) in methanol (150 ml) and acetic acid (1.5 ml). The clear reaction mixture was stirred at room temperature under argon for 2 hours and concentrated in vacuo. The residue was cooled in an ice bath, neutralized with saturated $NaHCO_3$ and extracted ($3\times$) with ethyl acetate. The organic phase was dried ($Na_2SO_4$), filtered and evaporated to give a pale yellow residue, which was purified by column chromatography on silica gel using 20% ethyl acetate-hexane. The title compound (8.4 g) was obtained as a pale yellow oil.

Step B. Preparation of N-(3-methyl-2(S)-(t-butoxycarbonylamino)but-1-yl)phenylalanine A solution of lithium hydroxide (1.63 g, 0.068 mole) in water (70 ml) was added to a solution of the product of Step A (7.6 g, 0.021 mole) in ethylene glycol dimethyl ether (100 ml) with cooling in an ice bath. The reaction mixture was stirred at room temperature under Ar for 2 hours, concentrated in vacuo, and extracted ($2\times$) with ethyl acetate. The aqueous phase was neutralized with 10% of citric acid, cooled and filtered to give the product as a white solid (6.6 g), mp>193° (dec).

Step C. Preparation of N-(3-methyl-2(S)-(t-butoxycarbonylamino)but-1-yl)phenylalanyl-methionine N-Methyl morpholine (4.0 ml) and 1-ethyl-3-(3-dimethylaminopropyl) carbodimide (EDC) hydrochloride (0.96 g, 0.005 mole) were added to a solution of the product of Step B (1.76 g, 0.005 mole), methionine methyl ester hydrochloride (1.0 g, 0.005 mole) and 1-hydroxybenzotriazole hydrate (HOBT, 0.677 g, 0.005 mole) in dimethylformamide (DMF, 30 ml) the reaction mixture was stirred at room temperature over the weekend, concentrated in vacuo and taken up in ice, water, and ethyl acetate. After addition of 10% aqueous citric acid, the ethyl acetate solution was separated, washed with water ($2\times$), aqueous $NaHCO_3$ and brine, and dried over sodium sulfate. Filtration and evaporation of the ethyl acetate solution gave a pale yellow residue, which was purified by column chromatography (silica gel) using 35% ethyl acetate-hexane. The title compound (1.97 g) was obtained as a white solid.

Step D. Preparation of N-(3-methyl-2(S)-aminobut-1-yl)phenylalanyl-methionine hydrochloride The product of Step C (0.74 g, 0.0015 mole) in ethyl acetate (25 ml) was treated with HCl gas at −25° C. for 30 min. The solution was stirred at room temperature for 1 hour and concentrated in vacuo to provide the title compound as a white solid (∼0.79 g).

Step E. Preparation of N-(3-methyl-2(S)-((N-t-butoxycarbonyl-S-triphenylmethylcysteinyl)amino)but-1-yl)phenylalanyl-methionine methyl ester N-Methylmorpholine (1.0 ml) and EDC (0.29 g, 0.0015 mole) were added to a solution of N-t-butoxycarbonyl-S-triphenylmethylcysteine (0.7 g, 0.0015 mole), the crude product of Step D (0.79 g, 0.0015 mole) and HOBT (0.18 g, 0.0013 mole) in 10 mL of DMF. The reaction mixture was stirred at room temperature under argon overnight, concentrated in vacuo and taken up in ice water and ethyl acetate. After addition of 10% aqueous citric acid, the ethyl acetate solution was separated, washed with water (2X), aqueous NaHCO$_3$ and brine, and dried over sodium sulfate. Filtration and evaporation of the ethyl acetate solution gave a pale yellow oily residue, which was purified by column chromatography (silica gel) using 40% ethyl acetate/hexane. The product was obtained as a white foam (1.13 g).

Step F. Preparation of N-(3-methyl-2(S)-((N-t-butoxycarbonyl-S-triphenylmethylcysteinyl)amino)but-1-yl)phenylalanyl-methionine The product of Step E (0.96 g, 1.14 mmol) in methanol (25 ml) was treated with a solution of lithium hydroxide (0.11 g, 0.0046 mole) in 10 ml of water. The reaction mixture was stirred at room temperature under Ar for 3 hours, diluted with water and filtered. The filtrate was neutralized with 10% aqueous citric acid, cooled and filtered to give the product as a white solid (0.86 g).

Step G. Preparation of N-(3-methyl-2(S)-(cysteinylamino)butyl)-phenylalanyl-methionine Triethylsilane (0.4 ml, 0.025 mole) was added to a solution of the product of Step F (0.86 g, 0.001 mole) in methylene chloride (15 ml) and trifluoroacetic acid (7 ml). The reaction mixture was stirred at room temperature under Ar for 2 hours and concentrated in vacuo. The residue was triturated with ether and the mixture was filtered to obtain a white solid, which was purified by preparative reverse phase HPLC using gradient elution with acetonitrile-water containing 0.1% trifluoroacetic acid. Lyophilization of the appropriate fractions gave the title compound as a white solid.

$^1$H NMR (CD$_3$OD) δ7.32 (5H, m), 4.45 (1H, dd, J=4.7, 9.0 Hz), 4.02 (2H, m), 3.95 (1H, m), 3.22 (1H, dd, J=7.3, 14.0 Hz), 3.14 (2H, m), 3.03 (1H, dd, J=5.0, 15.0 Hz), 2.99 (m, 1H), 2.94 (1H, dd, J=7.3, 15.0 Hz), 2.47 (1H, m), 2.35 (1H, m), 2.15 (1H, m), 2.06 (3H, s), 1.99 (1H, m), 1.89 (1H, m), 0.95 (3H, d, J=7.0), 0.94 (3H, d, J=7.0 Hz).

Anal. Calcd for C$_{22}$H$_{36}$N$_4$O$_4$S$_2$•2CF$_3$COOH•H$_2$O: C, 42.73; H, 5.52; H, 7.67. Found: C, 42.44; H, 5.24; H, 7.80.

EXAMPLE 2

Preparation of N-(3-methyl-2(S)-(mercaptopropionylamino)but-1-yl)phenylalanyl-methionine Using the methods of Example 1, except substituting 3-triphenylmethylmercaptopropionic acid for N-t-butoxycarbonyl-S-trityl cysteine in Step E, the title compound was obtained.

$^1$H NMR (CD$_3$OD) δ7.34 (5H, m), 4.48 (1H, dd, J=4.7, 9.4 Hz), 4.08 (1H, t, J=6.8 Hz), 3.85 (1H, ddd, J=2.6, 5.9, 9.0 Hz), 3.28 (1H, dd, J=6.4, 13.8 Hz), 3.20 (1H, dd, J=2.7, 12.6 Hz), 3.13 (1H, dd, J=7.2, 14.0 Hz), 2.85 (1H, dd, J=9.4, 12.8 Hz) 2.70 (2H, m), 2.53 (2H, t, J=6.7 Hz), 2.49 (1H, m), 2.39 (1H, dt, J=7.8, 7.8, 13.2 Hz), 2.18 (1H, m), 2.07 (3H, s), 1.99 (1H, m), 1.82 (1H, m), 0.94 (3H, d, J=12.5 Hz), 0.93 (3H, d, J=12.5 Hz).

Anal. Calcd. for C$_{22}$H$_{35}$N$_3$O$_4$S$_2$•1.2 CF$_3$COOH: C, 48.32; H, 6.02; N, 6.93. Found: C, 48.23; H, 6.13; H, 7.13.

EXAMPLE 3

Preparation of N-(3-mercaptopropyl)isoleucyl-phenylalanyl-methionine trifluoroacetate Step A. 3-triphenylmethylmercaptopropanal This compound was synthesized via the N-methoxy-N-methyl amide of 3-triphenylmethylmercaptopropionic acid according to the procedure of Goel, Krolls, Stier, and Kesten, Org. Syn. 67, 69–74 (1988). The compound was obtained as a white solid and used without purification in the subsequent reaction.

$^1$H NMR (CDCl$_3$) δ2.38 (m, 2H), 2.45 (m, 2H), 7.28 (m, 9H), 7.42 (m, 6H), 9.64 (s, 1H).

Step B. Preparation of isoleucyl-phenylalanyl methionine ethyl ester

This tripeptide was synthesized using standard peptide coupling methods beginning with methionine ethyl ester and adding Boc-protected amino acids with EDC and HOBT or HOOBT as condensing agents.

Step C. Preparation of N-(3-triphenylmethylmercaptopropyl)isoleucyl-phenylalanyl-methionine ethyl ester A solution of 253 mg of 3-triphenyl methylmercaptopropanal, prepared in Step A, and isoleucyl-phenylalanyl-methionine ethyl ester hydrochloride (375 mg) was prepared in a mixture of tetrahydrofuran and ethanol. 3 Å molecular sieves (508 mg) and 400 μl of 1M sodium cyanoborohydride in tetrahydrofuran were added. After 5 h the reaction mixture was filtered through Celite and the filtrate was concentrated in vacuo. The residual oil was dissolved in ethyl acetate and washed with water and brine. Chromatography on silica gel gave the title compound as a solid.

Step D. Preparation of N-(3-mercaptopropyl)isoleucylphenylalanyl-methionine trifluoroacetate The triphenylmethyl protecting group of the product of Step C was removed using the method of Example 1, Step G. The ethyl ester was then hydrolyzed according to the method of Example 1, Step F, under an argon atmosphere. The crude product was purified using reverse-phase preparative HPLC, eluting with acetonitrile/water/0.1% trifluoroacetic acid. The title compound was isolated after lyophilization as a white solid, m.p. 212°–225°

$^1$H NMR (CD$_3$OD+DMSO-d$_6$) δ0.95 (m, 6H), 1.23 (m, 1H), 1.63 (m, 1H), 1.78 (m, 2H), 1.88 (m, 1H), 1.98 (m, 1H), 2.10 (s, 3H), 2.18 (m, 1H), 2.40–2.70 (m, 6H), 2.90 (dd, 1H), 3.25 (dd, 1H), 3.60 (d, 1H), 4.58 (m, 1H), 4.92 (m, 1H), 7.25 (m, 1H), 7.32 (m, 4H).

Anal. Calcd for C$_{23}$H$_{37}$N$_3$O$_4$S$_2$•1.35 CF$_3$CO$_2$H: C, 48.41; H, 6.06; N, 6.59. Found: C, 48.39; H, 6.13; N, 6.59.

EXAMPLE 4

Preparation of N-(2(R)-amino-3-mercaptopropyl)isoleucyl-phenylalanyl-methionine

Step A. Preparation of N-(t-butoxycarbonyl)-S-trityl cysteine aldehyde

This compound was synthesized by applying the procedure of Goel, Krolls, Stier, and Kesten to N-(t-butoxycarbonyl)-S-trityl cysteine. The compound was obtained as a white solid, which was used without purification.

$^1$H NMR (CDCl$_3$) δ9.2 (1H, s), 7.5–7.1 (18H, m), 5.1 (1H, br d), 3.92 (1H, m), 2.85–2.5 (2H, m), 1.4 (9H, s).

Step B. Preparation of N-(2(R)-amino-3-mercaptopropyl)isoleucyl-phenylalanyl-methionine Using the method of Example 3, except using N-(t-butoxycarbonyl)-S-trityl cysteine aldehyde in place of 3-triphenyl methylmercaptopropanal in Step C, the title compound was prepared.

$^1$H NMR (CD$_3$OD) δ0.70 (d, 3H), 0.83 (t, 3H), 1.06 (m, 1H), 1.40–1.58 (m, 2H), 1.98 (m, 1H), 2.08 (s, 3H), 2.18 (m, 1H), 2.48–2.68 (m, 5H), 2.76 (dd, 1H), 2.88 (dd, 2H), 3.20 (m, 1H), 3.25 (dd, 1H), 4.58 (dd, 1H), 7.21 (m, 1H), 7.30 (m, 4H).

Anal. Calcd for C$_{23}$H$_{38}$N$_4$O$_4$S$_2$•2 CF$_3$CO$_2$H•1.64 H$_2$O: C, 42.88; H, 5.77; N, 7.41. Found: C, 42.85; H, 5.68; N, 7.48.

EXAMPLE 5

According to the methods described in Examples 3 and 4, but using the tripeptide valyl-isoleucyl-methionine methyl ester the following compound was prepared.

N-(3-mercaptopropyl)valyl-isoleucyl-methionine, mp>250.

$^1$H NMR (CD$_3$OD) δ0.94 (t, 3H), 1.03 (m, 6H), 1.10 (d, 3H), 1.25 (m, 1H), 1.63 (m, 1H), 1.84–2.03 (m, 4H), 2.08 (s, 3H), 2.18 (m, 2H), 2.46–2.64 (m, 4H), 3.08 (t, 2H), 3.72 (d, 1H), 4.32 (d, 1H), 4.58 (dt, 1H).

Anal. Calcd for C$_{19}$H$_{37}$N$_3$O$_4$S$_2$•CF$_3$CO$_2$H: C, 45.89; H, 6.97; N, 7.64. Found: C, 45.95; H, 6.98; N, 7.42. Methyl ester:

Anal. Calcd for C$_{20}$H$_{39}$N$_3$O$_4$S$_2$•0.5 H$_2$O: C, 52.29; H, 8.79; N, 9.15. Found: C, 52.33; H, 8.67; N, 8.92.

EXAMPLE 6

According to the methods described in Examples 3 and 4, but using the tripeptide valyl-isoleucyl-methionine methyl ester, the following compound was prepared.

N-(2(R)-amino-3-mercaptopropyl)valyl-isoleucyl-methionine.

$^1$H NMR (CD$_3$OD) δ0.93 (t, 3H), 1.0 (m, 9H), 1.22 (m, 1H), 1.60 (m, 1H), 1.85–2.03 (m, 3H), 2.08 (s, 3H), 2.14–2.22 (m, 1H), 2.48–2.64 (m, 2H), 2.72–2.92 (m, 5H), 4.32 (d, 1H), 4.62 (m, 1H).

Anal. Calcd for C$_{19}$H$_{38}$N$_4$O$_4$S$_2$•2CF$_3$CO$_2$H: C, 40.70; H, 5.94; N, 8.25. Found: C, 40.76; H, 6.15; N, 8.63.

EXAMPLE 7

Preparation of N-[2(S)-(2(R)-amino-3-mercaptopropylamino)-3(S)-methyl]pentyl-phenylalanyl-methionine Step A. Preparation of N-(t-butoxy carbonyl) isoleucine aldehyde This compound was synthesized by applying the procedure of Goel, Krolls, Stier, and Kesten to N-(t-butoxycarbonyl) isoleucine hemihydrate. The compound was obtained as an oil and used without purification.

$^1$H NMR (CDCl$_3$) δ0.94–1.0 (m, 6H), 1.20–1.32 (m, 1H), 1.40–1.51 (m, 1H), 1.45 (s, 9H), 2.02 (m, 1H), 4.28 (m, 1H), 5.13 (br s, 1H), 9.67 (s, 1H).

Step B. Preparation N-[2(S)-(t-butoxycarbonylamino)-3(S)-methyl]pentyl-phenylalanine methyl ester N-(t-butoxycarbonyl)isoleucine aldehyde (5.0 g) and phenylalanine methyl ester hydrochloride (5 g) were dissolved in a mixture of anhydrous tetrahydrofuran (THF, 80 ml), ethyl acetate (10 ml), and anhydrous ethanol (20 ml). 3 Å molecular sieves were added followed by 34.8 ml of 1M sodium cyanoborohydride in THF. Anhydrous ethanol (30 ml) and 1.33 ml (1 equiv.) of acetic acid were added. After 2.5 hours the reaction mixture was filtered through celite and the filtrate was concentrated in vacuo. The oil residue was partitioned between ethyl acetate and saturated sodium bicarbonate solution. The organic phase was washed with brine, dried (Na$_2$SO$_4$), filtered, and concentrated in vacuo to an oil residue. Chromatography on silica gel gave the title compound as an oil. $^1$H NMR spectroscopy indicates that this is a 2:1 mixture of diastereomers based on the integration of two singlets for the methyl ester protons at 3.65 ppm and 3.68 ppm in CDCl$_3$.

Step C. Preparation of N-[2(S)-(t-butoxycarbonyl amino)-3(S)-methyl]pentyl-phenylalanine The product of Step B was hydrolyzed as described in Example 1, Step F.

Step D. Preparation of N-[2(S)-(t-butoxycarbonyl amino)-3(S)-methyl]pentyl-phenylalanylmethionine The solid product of Step C was dissolved in dimethylformamide (25 ml) with HOBT (1.07 g). Methionine methyl ester hydrochloride (1.58 g) was added followed by EDC (1.67 g). After a solution was obtained, triethylamine (2.3 ml) was added slowly. After 2 hours the solvent was removed in vacuo and the residue was partitioned between ethyl acetate and saturated sodium bicarbonate. The organic phase was washed with brine, dried (Na$_2$SO$_4$), filtered, and concentrated in vacuo to give a waxy solid. Chromatography on silica gel gave the title compound contaminated with a stereoisomer.

Step E. Preparation of N-[2(S)amino)-3(S)-methyl-pentyl]phenylalanyl-methionine hydrochloride The product of Step D was converted to the title compound by the method of Example 1, Step D.

Step F. Preparation of N-[2(S)-(2(R)-t-butoxycarbonylamino-3-triphenylmethylmercaptopropylamino)-3(S)-methylpentyl]phenylalanyl-methionine methyl ester The hydrochloride salt (195 mg), prepared in Step E, was dissolved in anhydrous ethanol (2 ml) and diisopropyl ethyl amine was added to obtain a pH of 8.0. A 167 mg sample of N-(t-butoxy carbonyl)-S-trityl-cysteine aldehyde, prepared in Example 4, Step A, was dissolved in ethanol and added to the above solution along with 3 Å molecular sieves and 14 mg of sodium cyanoborohydride. After 16 hours the reaction mixture was filtered and the filtrate was concentrated in vacuo and partially purified by preparative reverse phase HPLC (acetonitrile/water/0.1% TFA). Further purification by silica gel chromatography gave the title compound as a white solid.

Step G. Preparation of N-[2(S)-(2(R)-t-butoxycarbonylamino-3-triphenylmethylmercaptopropylamino)-3(S)-methylpentyl]phenylalanyl-methionine The product of Step F was hydrolyzed as described in Example 1, Step F.

Step H. Preparation of N-[2(S)-(2(R)-amino-3-mercaptopropylamino)-3(S)-methyl]pentyl-phenylalanyl-methionine The product of Step G was converted to the title compound using the method of Example 1, Step G. $^1$H NMR (CDCl$_3$) δ0.84 (d, 3H), 0.95 (t, 3H), 1.22 (m, 1H), 1.34 (m, 1H), 1.78 (m, 1H), 1.98 (m, 1H), 2.05 (s, 3H), 2.12 (m, 1H), 2.28 (m, 1H), 2.42 (m, 1H), 2.70–2.90 (m, 5H), 3.02 (m, 2H), 3.22 (m, 1H), 4.12 (t, 1H), 4.41 (dd, 1H), 7.30 (m, 5H).

Anal. Calcd for C$_{23}$H$_{40}$N$_4$O$_3$S$_2$•2.5 CF$_3$CO$_2$H: C, 43.52; H, 5.53; N, 7.22. Found: C, 43.58; H, 5.45; N, 7.07.

EXAMPLE 8

Preparation of N-[2(S)-(3-mercaptopropyl amino-3(S)-methyl]pentyl-phenylalanyl-methionine The title compound was prepared using the methods of Example 7, except substituting 3-triphenylmethylthiopropanal for the N-(t-butoxy carbonyl)-S-trityl-cysteine aldehyde used in Step F.

$^1$H NMR (CDCl$_3$) δ1.10 (d, 3H); 1.18 (t, 3H); 1.34 (m, 1H); 1.65 (m, 1H); 2.02 (m, 1H); 2.08–2.25 (m, 3H); 2.30 (s, 3H); 2.40 (m, 1H); 2.62 (m, 1H); 2.72 (m, 1H); 2.78 (m, 2H); 2.95 (m, 1H); 3.11 (m, 2H); 3.52 (s, 1H); 3.80 (m, 1H); 4.72 (m, 1H); 7.50 (m, 5H).

Anal. Calcd for C$_{23}$H$_{39}$N$_3$O$_3$S$_2$•1.86 CF$_3$CO$_2$H: C, 47.07; H, 6.04; N, 6.16. Found C, 47.07; H, 6.02; N, 6.29.

EXAMPLE 9

Using the methods of Example 1-8, substituting the appropriate protected amino acids and aldehydes, the following compounds were obtained:

(A) N-(2(R)-amino-3-mercaptopropyl)isoleucyl-phenylalanyl-(methionine sulfone) was prepared via coupling of N-(2(R)-t-butoxycarbonylamino-3-triphenylmethylmercaptopropyl)-isoleucine with phenylalanyl-methionine sulfone methyl ester, mp 84–88.

Anal. Calcd for C$_{23}$H$_{38}$N$_4$O$_6$S$_2$: C, 41.27; H, 5.52; N, 7.13. Found: C, 41.15; H, 5.19; N, 7.07.

(B) N-(2(R)-amino-3-mercaptopropyl)isoleucyl-(p-iodophenylalanyl)-methionine was prepared via reductive alkylation of isoleucyl-(p-iodophenylalanyl)methionine methyl ester, mp 100–115.

Anal. Calcd for C$_{23}$H$_{37}$IN$_4$O$_4$S$_2$•1.7 CF$_3$COOH: C, 38.74; H, 4.77; N, 6.85. Found: C, 38.69; H, 4.72; N, 6.99.

(C) N-[2(R)-(cysteinyl-isoleucylamino)-3(S)-methyl-pentyl]methionine was prepared via coupling of N-t-butoxycarbonyl-S-triphenylmethylcysteinylisoleucine with N-[2(R)-amino-3(S)-methylpentyl]methionine methyl ester.

Anal. Calcd for C$_{20}$H$_4$ON$_4$O$_4$S$_2$•2 CF$_3$COOH: C, 41.61; H, 6.11; N, 8.09. Found: C, 41.38; H, 6.18; N, 8.47.

(D) N-[2(R)-(N'-(2(R)-amino-3-mercaptopropyl)isoleucylamino)-3-phenyl-propyl]methionine was prepared via coupling of N-(2(R)-t-butoxycarbonylamino-3-triphenylmethylmercaptopropyl)isoleucine with N-[2(R)-amino-3-phenylpropyl]methionine methyl ester.

Anal. Calcd for C$_{23}$H$_{40}$N$_4$O$_3$S$_2$•2.8 CF$_3$COOH: C, 42.72; H, 5.37; N, 6.97. Found: C, 42.73; H, 5.60; N, 7.27.

(E) N-[2(R)-(N'-(2(R)-amino-3-mercaptopropyl)isoleucylamino)-3(S)-methyl-pentyl]methionine was prepared via coupling of N-(2(R)-t-butoxycarbonylamino-3-triphenylmethylmercaptopropyl)isoleucine with N-[2(R)-amino-3(S)-methylpentyl]methionine methyl ester.

Anal. Calcd for C$_{20}$H$_{42}$N$_4$O$_3$S$_2$•2.7 CF$_3$COOH: C, 40.22; H, 5.94; N, 7.39. Found: C, 39.87; H, 5.79; N, 7.72.

(F) N-(2(R)-amino-3-mercaptopropyl)isoleucyl-phenylalanyl-methionine ethyl ester was prepared by reductive alkylation of isoleucyl-phenylalanylmethionine ethyl ester.

Anal. Calcd for C$_{25}$H$_{42}$N$_4$O$_4$S$_2$•2 CF$_3$COOH: C, 45.66; H, 5.93; N, 7.34. Found: C, 45.69; H, 5.71; N, 6.96.

(G) N-(3-phenyl-2(S)-(mercaptopropionylamino)-prop-1-yl)isoleucyl-methionine was prepared by coupling resin-bound methionine to N-(3-phenyl-2(S)-t-butoxycarbonylaminopropyl)isoleucine followed by deprotection, coupling with a protected cysteine and further processing under standard solid phase synthesis conditions. FAB MS m/z 484 (M+1).

(H) N-(2(R)-amino-3-mercaptopropyl)isoleucyl-phenylalanyl-methionine benzyl ester was prepared by reductive alkylation of isoleucyl-phenylalanylmethionine benzyl ester, mp 71°–78° C.

Anal. Calcd for C$_{30}$H$_{44}$N$_4$O$_4$S$_2$•1.6 CF$_3$COOH: C, 51.57; H, 5.94; N, 7.23. Found: C, 51.52; H, 5.86; N, 7.42.

EXAMPLE 10

In vivo ras farnesylation assay

The cell line used in this assay was the v-ras line, which expressed viral Ha-ras p21. The assay was performed essentially as described in DeClue, J. E. et. al., Cancer Research 51, 712–717, (1991). Cells in 10 cm dishes at 50–75% confluency were treated with the test compound (final concentration of solvent, methanol or dimethyl sulfoxide, was 0.1%). After 4 hours at 37° C., the cells were labelled in 3 ml methionine-free DMEM supplemented with 10% regular DMEM, 2% fetal bovine serum and 400 μCi[$^{35}$S]methionine (1000 Ci/mmol). After an additional 20 hours, the cells were lysed in 1 ml lysis buffer (1% NP40/20 mM HEPES, pH 7.5/5 mM MgCl$_2$/1 mM DTT/10 μg/ml aprotinen/2 μg/ml leupeptin/2 μg/ml antipain/0.5 mM PMSF) and the lysates cleared by centrifugation at 100,000×g for 45 min. Aliqouts of lysates containing equal numbers of acid-precipitable counts were bought to 1 ml with IP buffer (lysis buffer lacking DTT) and immunoprecipitated with the ras-specific monoclonal antibody Y13-259 (Furth, M. E. et. al., J. Virol. 43, 294–304, (1982)). Following a 2 hour antibody incubation at 4° C., 200 μl of a 25% suspension of protein A-Sepharose coated with rabbit anti rat IgG was added for 45 min. The immunoprecipitates were washed four times with IP was buffer (20 nM HEPES, pH 7.5/1 mM EDTA/1% Triton X-100.0.5% deoxycholate/0.1%/SDS/0.1M NaCl) boiled in SDS-PAGE sample buffer and loaded on 13% acrylamide gels. When the dye front reached the bottom, the gel was fixed, soaked in Enlightening, dried and autoradiographed. The intensities of the bands corresponding to farnesylated and nonfarnesylated ras proteins were compared to determine the percent inhibition of farnesyl transfer to protein.

TABLE 1

Inhibition of Ras Farnesylation by the compounds of the invention in the v-ras cell line

| Compound | Inhibition |
| --- | --- |
| N-[2(S)-(2(R)-amino-3-mercaptopropyl-amino)-3(S)-methylpentyl]phenyl-alanyl-methionine | 30% inhibition at 100 μm test concentration |
| N-2(R)-amino-3-mercaptopropyl)iso-leucyl-phenylalanyl-methionine ethyl ester | 10% inhibition at 10 μm test concentration |

EXAMPLE 11

In vitro inhibition of Ras Farnesyl Transferase

Farnesyl-protein transferase (FTase) from bovine brain was chromatographed on DEAE-Sephacel (Pharmacia, 0–0.8M NaCl gradient elution), N-octyl agarose (Sigma, 0–0.6M NaCl gradient elution), N-octyl agarose (Sigma, 0–0.6M NaCl gradient elution), and a mono Q HPLC column (Pharmacia, 0–0.3M NaCl gradient). Ras-CVLS at 3.5 μM, 0.25 μM [$^3$H]FPP, and the indicated compounds were incubated with this partially purified enzyme preparation. The FTase data presented below is a measurement of the ability of the test compound to inhibit Ras farnesylation in vitro.

TABLE 2

Inhibition of Ras Farnesylation by the compounds of this invention

| Compound | IC$_{50}$* (nM) |
|---|---|
| N-[2(S)-(2(R)-amino-3-mercaptopropyl-amino)-3(S)-methylpentyl]phenylalanyl-methionine | 4.7 |
| N-(3-methyl-2(S)-(cysteinylamino)-but-1-yl)phenylalanyl-methionine | 7 |
| N-2(R)-amino-3-mercaptopropyl)iso-leucyl-phenylalanyl-methionine ethyl ester | 2000 |

*(IC$_{50}$ is the concentration of compound which gives 50% inhibition of FTase under the described assay conditions)

What is claimed is:

1. A compound which inhibits farnesylprotein transferase of the formula:

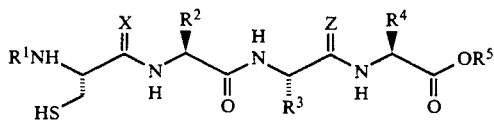

wherein:
X, Y and Z are independently H$_2$ or O, provided that at least one of these is H$_2$;
R$^1$ is H, an alkyl group, an acyl group, an alkylsulfonyl group or arylsulfonyl group, wherein alkyl and acyl groups comprise straight chain or branched chain hydrocarbons of 1 to 6 carbon atoms, or in the alternative, R$^1$NH may be absent;
R$^2$, R$^3$ and R$^4$ are the side chains of naturally occurring amino acids, or in the alternative may be substituted or unsubstituted aliphatic, aromatic or heteroaromatic groups, wherein the aliphatic substitutents may be substituted with an aromatic or heteroaromatic ring;
R$^5$ is H or a straight or branched chain aliphatic group, which may be substituted with an aromatic or heteroaromatic group;
or the pharmaceutically acceptable salts thereof.

2. The compound of claim 1, wherein the compound is:
N-(3-phenyl-2(S)-(mercaptopropionylamino)prop-1-yl)isoleucyl-methionine,
N-(2(R)-amino-3-mercaptopropyl)isoleucyl-phenyl-alanyl-methionine,
N-(3-mercaptopropyl)isoleucyl-phenylalanyl-methionine,
N-(3-mercaptopropyl)valyl-isoleucyl-methionine,
N-(2(R)-amino-3-mercaptopropyl)valyl-isoleucyl-methionine,
N-(3-methyl-2(S)-(cysteinylamino)but-1-yl)phenyl-alanyl-methionine,
N-(3-methyl-2(S)-(mercaptopropionylamino)but-1-yl)phenylalanyl-methionine,
N-[2(S)-(2(R)-amino-3-mercaptopropylamino)-3(S)-methylpentyl]phenylalanyl-methionine,
N-[2(S)-(3-mercaptopropylamino)-3(S)-methylpentyl]phenylalanyl-methionine,
N-(2(R)-amino-3-mercaptopropyl)isoleucyl-phenyl-alanyl-(methionine sulfone),
N-(2(R)-amino-3-mercaptopropyl)isoleucyl-(p-iodo-phenylalanyl)-methionine,
N-[2(R)-(cysteinyl-isoleucylamino)-3(S)-methylpentyl]methionine,
N-[2(R)-(N'-(2(R)-amino-3-mercaptopropyl)-isoleucylamino)-3-phenyl-propyl]methionine,
N-[2(R)-(N'-(2(R)-amino-3-mercaptopropyl)-isoleucylamino)-3(S)-methylpentyl]methionine,
N-(3-mercaptopropyl)valyl-isoleucyl-methionine methyl ester,
N-(2(R)-amino-3-mercaptopropyl)isoleucyl-phenyl alanyl-methionine ethyl ester, or
N-(2(R)-amino-3-mercaptopropyl)isoleucyl-phenyl-alanyl-methionine benzyl ester or the pharmaceutically acceptable salts thereof.

3. The compound of claim 1 which is:
N-[2(S)-(2(R)-amino-3-mercaptopropylamino)-3(S)-methylpentyl]phenylalanyl-methionine

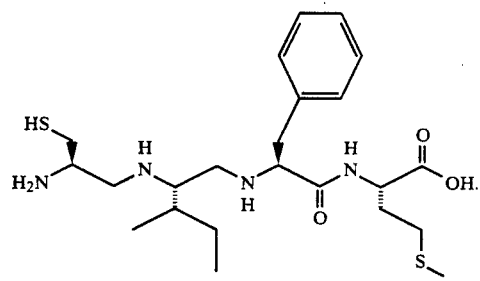

or the pharmaceutically acceptable salts thereof.

4. The compound of claim 1 which is:
N-(3-methyl-2(S)-(cysteinylamino)but-1-yl)phenylalanylmethionine

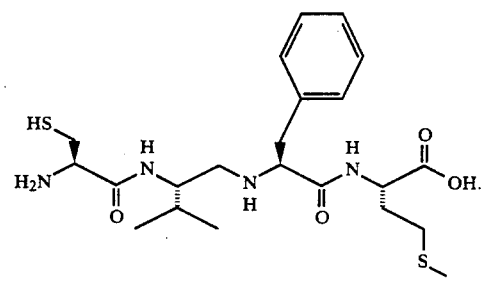

5. The compound of claim 1 which is:
N-(2(R)-amino-3-mercaptopropyl)isoleucyl-phenylalanyl-methionine ethyl ester

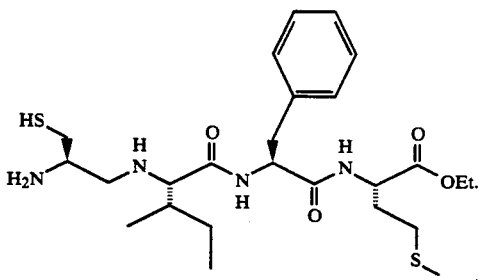

6. A chemotherapeutic composition comprising a pharamaceutical carrier, and dispersed therein, a therapeutically effective amount of a compound of claim 1.

7. A chemotherapeutic composition comprising a pharmaceutical carrier, and dispersed therein, a therapeutically effective amount of compound of claim 2.

8. A chemotherapeutic composition comprising a pharmaceutical carrier, and dispersed therein, a therapeutically effective amount of a compound of claim 3.

9. A chemotherapeutic composition comprising a pharmaceutical carrier, and dispersed therein, a therapeutically effective amount of a compound of claim 4.

10. A chemotherapeutic composition comprising a pharmaceutical carrier, and dispersed therein, a therapeutically effective amount of a compound of claim 5.

11. A method for inhibiting farnesylation of Ras protein which comprises administering to a mammal in need thereof a therapeutically effective amount of a composition of claim 6.

12. A method for inhibiting farnesylation of Ras protein which comprises administering to a mammal in need thereof a therapeutically effective amount of a composition of claim 7.

13. A method for inhibiting farnesylation of Ras protein which comprises administering to a mammal in need thereof a therapeutically effective amount of a composition of claim 8.

14. A method for inhibiting farnesylation of Ras protein which comprises administering to a mammal in need thereof a therapeutically effective amount of a composition of claim 9.

15. A method for inhibiting farnesylation of Ras protein which comprises administering to a mammal in need thereof a therapeutically effective amount of a composition of claim 10.

16. The method according to claim 11, wherein the mammal is a human.

17. The method according to claim 12, wherein the mammal is a human.

18. The method according to claim 13, wherein the mammal is a human.

19. The method according to claim 14, wherein the mammal is a human.

20. The method according to claim 15, wherein the mammal is a human.

21. The compound of claim 1, wherein the substituted or unsubstituted aliphatic, aromatic, or heteroaromatic groups are allyl, cyclohexyl, phenyl, pyridyl, or imidazolyl groups, or are saturated chains of 2 to 8 carbon atoms.

* * * * *

UNITED STATES PATENT AND TRADEMARK OFFICE
CERTIFICATE OF CORRECTION

Page 1 of 2

PATENT NO. : 5,238,922
DATED : August 24, 1993
INVENTOR(S): Graham et al.

It is certified that errors by the USPTO appear in the above-identified patent and that said Letters Patent is hereby corrected as shown below:

At Column 3, between lines 1-8, please replace the structure with the following:

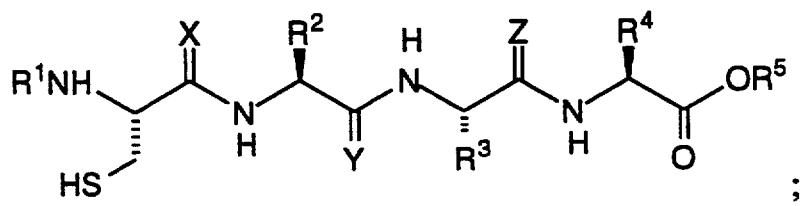

;

At Column 3, lines 15-22, please replace the structure with the following;

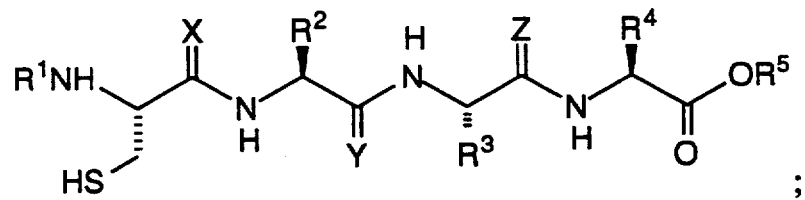

;

UNITED STATES PATENT AND TRADEMARK OFFICE
CERTIFICATE OF CORRECTION

PATENT NO. : 5,238,922
DATED : August 24, 1993
INVENTOR(S) : Graham, et. al.

It is certified that error appears in the above-indentified patent and that said Letters Patent is hereby corrected as shown below:

At Column 15, lines 30-36, please replace the structure with the following;

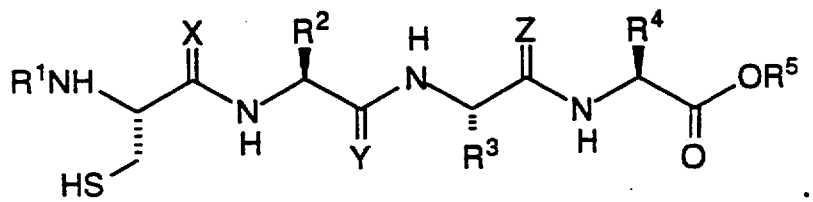

Signed and Sealed this

Seventh Day of March, 1995

Attest:

BRUCE LEHMAN

Attesting Officer    Commissioner of Patents and Trademarks